United States Patent [19]

Aoki et al.

[11] Patent Number: 4,994,279

[45] Date of Patent: Feb. 19, 1991

[54] MULTI-LAYER GRANULE

[75] Inventors: Shigeru Aoki, Gifu; Keizo Uesugi, Aichi; Shigeru Sakashita; Masayoshi Kasai, both of Gifu; Masanori Kayano, Saitama, all of Japan

[73] Assignee: Eisai Co., Ltd., Tokyo, Japan

[21] Appl. No.: 302,646

[22] Filed: Jan. 26, 1989

[30] Foreign Application Priority Data

Feb. 3, 1988 [JP] Japan ................... 63-23215

[51] Int. Cl.$^5$ ................................ A61K 9/50
[52] U.S. Cl. ..................... 424/494; 424/490; 424/493; 424/496; 424/498
[58] Field of Search ............... 424/494, 495, 493, 496, 424/498

[56] References Cited

U.S. PATENT DOCUMENTS

| T861,008 | 4/1969 | Butter | 424/494 |
|---|---|---|---|
| 2,921,883 | 1/1960 | Reese et al. | 424/494 X |
| 2,991,226 | 7/1961 | Millar et al. | 424/494 X |
| 3,577,512 | 10/1968 | Shephard et al. | 424/464 |
| 3,879,511 | 4/1975 | Goodhart et al. | 424/495 |
| 4,122,157 | 10/1978 | Huber | 424/472 |
| 4,138,475 | 2/1979 | McAinsh et al. | 424/494 |
| 4,155,993 | 5/1979 | Belleville et al. | 424/464 |
| 4,261,970 | 4/1981 | Ogawa et al. | 424/490 |
| 4,309,405 | 1/1982 | Guley et al. | 424/480 |
| 4,309,406 | 1/1982 | Guley et al. | 424/480 |
| 4,404,183 | 9/1983 | Kawata et al. | 424/4 |
| 4,454,108 | 6/1984 | Iida et al. | 424/464 |
| 4,483,846 | 11/1984 | Koide et al. | 604/890 X |
| 4,552,751 | 11/1985 | Inaba et al. | 514/443 |
| 4,568,536 | 2/1986 | Kronenthal et al. | 514/772 |
| 4,572,883 | 2/1986 | Pedersen et al. | 427/3 |
| 4,600,645 | 7/1986 | Ghebre-Sellassie et al. | 428/403 |
| 4,609,542 | 9/1986 | Panoz et al. | 514/192 |
| 4,634,587 | 1/1987 | Hsiao | 424/495 |
| 4,708,874 | 11/1987 | DeHaan et al. | 424/470 |
| 4,729,895 | 3/1988 | Makino et al. | 424/495 X |
| 4,808,416 | 2/1989 | Hata et al. | 424/494 |

FOREIGN PATENT DOCUMENTS

| 0074584 | 3/1983 | European Pat. Off. . |
|---|---|---|
| 0220670 | 5/1987 | European Pat. Off. . |
| 2721603 | 5/1976 | Fed. Rep. of Germany . |
| 3403329 | 8/1985 | Fed. Rep. of Germany ...... 424/494 |
| 2404029 | 4/1979 | France . |
| 0935602 | 8/1963 | United Kingdom ............... 424/494 |

OTHER PUBLICATIONS

"Stearate" Definition: Hackh's Chemical Dictionary—4th Edition, Ed.—Julius Grant.

*Primary Examiner*—Thurman K. Page
*Attorney, Agent, or Firm*—Flynn, Thiel, Boutell & Tanison, P.C.

[57] ABSTRACT

A multi-layered granule comprises an inner, slow-releasing layer, an outer, rapid-releasing layer and an intermediate layer provided between said slow-releasing layer and said rapid-releasing layer which intermediate layer comprises a hardened oil and hydroxypropyl cellulose or methyl cellulose.

9 Claims, No Drawings

MULTI-LAYER GRANULE

This invention relates to a multi-layer granule comprising a slow release layer and a rapid release layer outwardly surrounding the slow release layer, and more particularly to a multi-layer granule in which the slow release part and the rapid release part are integrated in such a way that the effective component(s) can be released over a prolonged period of time.

THE PRIOR ART

During treatment with drugs, it is frequently required to sustain an adequate therapeutic concentration of the drug in the living body over a period of time. Sustained action preparations have been designed for this purpose. These are divided into a number of different types and devised from various aspects. In some cases, preparations are useful which comprise rapid and slow release parts so that in the living body, effective blood concentration levels of the drug may be achieved early and maintained. As examples of such preparations are mentioned hard capsule type comprising slow and rapid release granules previously prepared, respectively, mixed and charged together in a hard capsule, and multi-layer granule type disclosed in Japanese laid-open patent No. 103012/1987 applied by the present inventors.

The above-mentioned conventional sustainied release drugs however do not fully meet all requirements. The difficulties with slow release are, for instance, some are dissolved with a remarkable variation dependent on the pH of the solvent (in vitro), and that some which utilize a low melting point wax for the purpose of slow release may lose the slow release characteristics during storage at high temperature (45° C.).

SUMMARY OF THE INVENTION

Under these circumstances, the inventors searched for a base or vehicle of a drug which was substantially unaffected by the pH of a solvent and permitted the slow release characteristic to be remain unaffected during high temperature storage, and, as a result, hardened oil has been found to be adequate as such a base. It was discovered that a membranous layer composed of a sucrose-fatty acid ester, talc, and ethyl cellulose had a lag time of at least 3 hours while the incorporation of hydroxypropyl cellulose or methyl cellulose as a water-path forming agent resulted in substantially no lag time. Thus the present invention has been accomplished.

It therefore is an object of the invention to provide a multi-layer granule comprising a slow release layer, a rapid release layer outwardly surrounding the slow release layer, and an intermediate membranous layer therebetween made essentially from a hardened oil and hydroxypropyl cellulose or methyl cellulose.

The invention provides a multi-layered granule comprising an inner, slow-releasing layer, an outer, rapid-releasing layer and an intermediate layer, provided between said slow-releasing layer and said rapid-releasing layer, which intermediate layer comprises a hardened oil and hydroxypropyl cellulose or methyl cellulose.

From the practical point of view, the granule of the invention comprises a core, an inner, slow-releasing layer comprising a pharmacologically effective ingredient, an outer, rapid-releasing layer comprising a pharmacologically effective ingredient and an intermediate layer, provided between said slow-releasing layer and said rapid-releasing layer, which intermediate layer comprises a hardened oil and hydroxypropyl cellulose or methyl cellulose.

It is preferable that the intermediate layer comprises 20 to 90 percent by weight of a hardened oil, 1 to 10 percent by weight of hydroxypropyl cellulose or methyl cellulose and the balance comprising a third component listed below.

Examples of hardened oils suitable for use in the present invention include hardened castor, rape and soybean oils. The membranous layer between the slow and rapid release layers is preferred to contain hardened oil within the range of 20 to 90% by weight, more preferably 20 to 80% by weight based on the total weight of the membranous layer.

A preferred content of hydroxypropyl cellulose or methyl cellulose suitable for use in the present invention is between 1 to 10% by weight based on the total weight of the membranous layer.

Multi-layer granules according to the invention can be produced with slow release granules as a starting material or with a granular seed. Suitable granular seeds (referred to as NPS) include generally-available granules formed of white sugar or a white sugar-corn starch mixture. The starting granule is, for instance, a pellet made by a process comprising kneading a mixture of medicine to be slowly-released and other ingredients together with a binder, and extruding the resultant mixture. The present invention is not limited to these processes. Seed may be used in a conventional way to form a slow release layer surrounding it.

Over the slow release layer is formed a membranous layer to be an intermediate layer which comprises essentially a hardened oil and hydroxypropyl cellulose or methyl cellulose as a coating. The coating may be applied by spraying a liquid preparation to be formed into the membranous layer while the subjects to be coated are flowing and rolling. The liquid preparation is prepared in a procedure consisting of the mixing of the above-mentioned essential ingredients with sucrose-fatty acid ester, talc, ethyl cellulose, etc. and dissolving or dispersing the resulting mixture in a solvent such as ethyl alcohol.

Over the resulting granules having the thus-formed membranous layer, a rapid release layer is formed. This may be done by the same method as in forming the intermediate membranous layer.

The thus-obtained multi-layer granular drugs may be used alone or in combination.

EXAMPLES

The invention will be described more fully by way of examples and is not limited by the examples.

EXAMPLE 1

NPS (2.87 kg), 28 to 32 mesh-sieved, granules were used as seed. Phenylpropanolamine hydrochloride (840 g), chlorpheniramine d-maleate (42 g), veradonna alkaroid (7 g), talc (290.5 g), light silicic acid anhydride (70 g), and hydroxypropyl cellulose (45.5 g), were dissolved and dispersed in ethyl alcohol (3 liter), and the resulting preparation was gradually fed into a small dish-revolving granulator (CF granulator), where seed granules were rolling, thus to form a layer (called R layer) over the seed granules, and dried at 45° C. by drafting for 12 hours. The obtained granules were called R granules.

Subsequently another preparation which was prepared by dissolving and dispersing a hardened oil (176 g) and talc (88 g), hydroxypropyl cellulose 9 g, ethyl cellulose 7.5 g, purified shellac (7.5 g) in a 1 liter of ethyl alcohol was gradually sprayed on R granules (1.19 kg) that were allowed to be rolling on the CF granulator to form a new layer (called C layer) and then dried at 40° C. with drafting for 12 hours. The obtained granules were termed C granules.

Subsequently, on the C granules (1428 kg), while rolling in the CF granulator, another preparation which was prepared by dissolving and dispersing phenylpropanolamine hydrochloride (320 g), lysozyme chloride (460 g), talc (200 g), light silicic acid anhydride (50 g), corn starch (442 g), and hydroxypropyl cellulose 100 g in 3.3 liter of ethyl alcohol was gradually sprayed to form further new layer (called I layer), and then dried at 40° C. with drafting for 12 hours. The thus-obtained granules were termed I granules.

Besides, on the C granules (1428 kg), while rolling in the CF granulator, another preparation which was prepared by dissolving and dispersing chlorpheniramine d-maleate (16 g), caffeine (600 g), dipotassium glycyrrhizate (300 g), light silicic acid anhydride (50 g), corn starch (686 g), and hydroxypropyl cellulose (70 g) in 3.3 liter of ethyl alcohol was gradually sprayed to form the new layer (called J layer), and then dried at 40° C. by drafting for 12 hours. The thus-obtained granules were termed J granules.

I granules and J granules made as described above were mixed in an 1:1 (weight:weight) ratio, and thus the multi-layer granules according to the present invention were obtained.

By reference, the composition of the obtained multi-layer granule, expressed in part by weight based on the entire weight of the granule, are as follows:

| | |
|---|---|
| Speed NPS | 82 |
| R layer: | |
| Phenylpropanolamine hydrochloride | 24 |
| Chlorpheniramine d-maleate | 1.2 |
| Veradonna alkaroid | 0.2 |
| Talc | 8.3 |
| Light silicic acid anhydride | 2 |
| Hydroxypropyl cellulose | 1.3 |
| C layer | |
| Hardened oil | 17.6 g, |
| Talc | 3.8 |
| Hydroxypropyl cellulose | 0.9 g |
| Ethyl cellulose | 0.75 |
| Purified shellac | 0.75 |
| I layer | |
| Phenylpropanolamine hydrochloride | 16 |
| Lysozyme chloride | 23 |
| Talc | 10 |
| Light silicic acid anhydride | 2.5 |
| Corn starch | 22.2 |
| Hydroxypropyl cellulose | 5 |
| J layer | |
| Chlorpheniramine d-maleate | 0.8 |
| Caffeine | 30 |
| Dipotassium glycyrrhizate | 30 |
| Light silicic acid anhydride | 10 |
| Corn starch | 31.8 |
| Hydroxypropyl cellulose | 3.5 |

EXAMPLE 2

This was conducted for making three different types of multi-layer granules (1), (2) and (3) according to the present invention in the same procedure as that of Example 1 except that the composition of the C layer of each type is respectively as described in the following (expressed part by weight):

| | (1) | (2) | (3) |
|---|---|---|---|
| C layer | | | |
| Hardened oil | 16.0 | 21.5 | 25.8 |
| Sucrose-fatty acid ester | 1.5 | 2 | 2.4 |
| Talc | 3.8 | 5 | 6 |
| Hydroxypropyl cellulose | 0.9 | 1.2 | 1.4 |
| Ethyl cellulose | 0.75 | 1 | 1.2 |
| Purified shellac | 0.75 | 1 | 1.2 |

Control 1

This was conducted for making another type of multi-layer granules in the same procedure as that of Example 1 except that the C layer has the following composition described below (expressed in part by weight):

| C layer | |
|---|---|
| Hardened oil | 14.8 |
| Sucrose-fatty acid ester | 8.4 |
| Talc | 10.8 |
| Ethyl cellulose | 1.8 |

EXAMPLE 3

This was conducted for making further three different types of multi-layer granules (4), (5) and (6) according to the present invention in the same procedure as that of Example 1 except that the composition of the C layer of each type was respectively as is described below (expressed in part by weight):

| C layer | (4) | (5) | (6) |
|---|---|---|---|
| Hardened oil | 7.4 | 7.4 | 7.4 |
| Sucrose-fatty acid ester | 4.2 | 4.2 | 4.2 |
| Talc | 2.7 | 2.7 | 8.1 |
| Methyl cellulose | 1.0 | 0.5 | — |
| Ethyl cellulose | 0.9 | 0.9 | 0.9 |

EXAMPLE 4

This was conducted for making further another type of multi-layer granules according to the present invention in the same procedure as that of Example 1 except that the C layer had the composition described below (expressed in part by weight):

| C layer | |
|---|---|
| Hardened oil | 19.2 |
| Sucrose-fatty acid ester | 1.8 |
| Talc | 4.5 |
| Hydroxypropyl cellulose | 1 |
| Ethyl cellulose | 0.9 |
| Purified shellac | 0.9 |

ADVANTAGES OF THE INVENTION

The advantages of the invention will become apparent from the tests described in the following.

Test 1

Multi-layer granules of types obtained in Example 1 and Control 1 were used as samples. Each sample was placed in a revolving basket (that in the Dissolution Test described in the Japanese Pharmacopoeia, 11 version), and immersed in the first solvent (the same Pharmacopoeia) for the first 2 hours. Thereafter dissolution proceeded by immersion in the second solvent (the same Pharmacopoeia). Dissolution percentages were determined by HPCL method.

The progresses in dissolution (represented by change in cumulative percentages with time) are summarized in Table 1.

TABLE 1

| Sample | Progresses in dissolution (cumulative percentage) Time (hours) | | | | | | |
|---|---|---|---|---|---|---|---|
| | 1 | 2 | 3 | 4 | 6 | 8 | 10 |
| Exampe 1 | 41.1 | 43.7 | 48.0 | 51.4 | 60.1 | 69.3 | 76.5 |
| Control 1 | 40.0 | 40.0 | 40.0 | 40.0 | 45.1 | 56.7 | 70.8 |

In Example 1, dissolution started substantially without lag time. On the other hand, Control 1 was done with lag time of at least 4 hours, and thus can not be regarded as good dissolution.

Test 2

Multi-layer granules of three types (C layer of each is (1), (2) and (3), respectively) according to the present invention obtained in Example 2 were used as samples. The changes in dissolution percentage with time were determined in the same way as in Test 1 as measured likewise by HPCL method.

The obtained results (as cumulative dilution percentages) were summarized in Table 2.

TABLE 2

| Sample | Progress in dissolution (cumulative percentage) Time (hours) | | | | | | |
|---|---|---|---|---|---|---|---|
| | 1 | 2 | 3 | 4 | 6 | 8 | 10 |
| (1) | 59.7 | 73.3 | 88.2 | 89.6 | 94.5 | 96.3 | 97.7 |
| (2) | 45.8 | 53.8 | 62.4 | 69.8 | 79.3 | 84.9 | 87.6 |
| (3) | 41.0 | 43.4 | 47.0 | 50.5 | 56.8 | 63.6 | 69.8 |

As apparent from Table 2, as to the multi-layer granules having a hardened oil-containing membrane layer according to the invention, the higher the content of hardened oil is, the slower the release becomes. Progress in dissolution therefore can be adjusted as desired by the modifying composition of the membrane layer.

Test 3

Multi-layer granules of three types (C layer of each is (4) and (5), respectively) according to the present invention, and control multi-layer granules (6) were used as samples. The progress in dissolution or change in dissolution percentage with time was determined in the same way as in Test 2.

The obtained results (as cumulative dilution percentages) were summarized in Table 3.

TABLE 3

| Sample | Progress in dissolution (cumulative percentage) Time (hours) | | | | | | |
|---|---|---|---|---|---|---|---|
| | 1 | 2 | 3 | 4 | 6 | 8 | 10 |
| (4) Invention | 43.3 | 51.8 | 65.8 | 77.3 | 84.9 | 94.3 | 99.0 |
| (5) Invention | 40.0 | 44.8 | 58.2 | 72.0 | 88.3 | 93.6 | 93.9 |
| (6) Control | 40.0 | 42.9 | 47.2 | 61.9 | 80.0 | 90.0 | 95.3 |

As apparent from Table 3, the methyl cellulose contained in the membrane layer according to the present invention can cause the lag time to reduce. The effect however is low when compared with that of hydroxypropyl cellulose.

Test 4

Multi-layer granules of the type obtained in Example 4 according to the present invention were used as samples. Sample portions were maintained at room temperature for one month, at 40° C. (RH 75%) for one month, and at 45° C. for one month, respectively, and then underwent a dissolution test in the same way as in Test 2.

The obtained results (as cumulative dilution percentages) were summarized in Table 4.

TABLE 4

| Stock conditions | Progress in dissolution (cumulative percentage) Time (hours) | | | | | | |
|---|---|---|---|---|---|---|---|
| | 1 | 2 | 3 | 4 | 6 | 8 | 10 |
| Room temp. | 57.0 | 65.4 | 71.3 | 76.1 | 83.4 | 89.5 | 92.5 |
| 40° C., RH 75% | 53.6 | 63.3 | 70.8 | 75.4 | 81.9 | 86.7 | 90.2 |
| 45° C. | 52.2 | 61.0 | 68.9 | 73.1 | 79.2 | 88.7 | 87.0 |

As revealed in Table 4, the membrane layer according to the invention keeps the protective effect on its release-regulation characteristic under different maintenance or storage conditions.

Test 5

Multi-layer granules of the type obtained in Example 4 were used as samples. By reference to the Dissolution Test described in the Japanese Pharmacopoeia (11 version), the sample portions were placed in a revolving basket and underwent dissolution (a) in the first solvent throughout the test period, (b) in the second solvent throughout the test period, and (c) in the first solvent for the first 2 hours and in the second solvent for the remaining hours of the test period, respectively.

The obtained results (as cumulative dilution percentages) are summarized in Table 5.

TABLE 5

| Extraction conditions | Progress in dissolution (cumulative percentage) Time (hours) | | | | | | |
|---|---|---|---|---|---|---|---|
| | 1 | 2 | 3 | 4 | 6 | 8 | 10 |
| (a) | 52.1 | 62.3 | 66.1 | 72.6 | 82.4 | 88.3 | 94.4 |
| (b) | 53.1 | 62.5 | 68.3 | 73.2 | 83.9 | 87.6 | 90.8 |
| (c) | 52.7 | 62.1 | 71.4 | 79.0 | 86.5 | 92.1 | 93.6 |

Table 5 demonstrates that the effect of the membranous layer according to the present invention on the release characteristic in independent of pH.

We claim:

1. A multi-layered granule comprising an inner slow-release layer containing a pharmacologically effective ingredient and adapted to release said pharmacologically effective ingredient at a first rate; an outer fast-release layer containing a pharmacologically effective ingredient and adapted to release said pharmacologically effective ingredient at a second rate which is greater than said first rate; and an intermediate layer provided between and in contact with said slow-release layer and said fast-release layer, said intermediate layer comprising a hardened oil and a cellulose selected from the group consisting of hydroxypropyl cellulose and methyl cellulose.

2. A granule as claimed in claim 1, wherein the intermediate layer comprises 20 to 90 percent by weight of a hardened oil and 1 to 10 percent by weight of hydroxypropyl cellulose or methyl cellulose.

3. A granule as claimed in claim 1, wherein said intermediate layer additonally comprises one or more members selected from the group consisting of a sucrose-fatty acid ester, talc and ethyl cellulose.

4. A granule as claimed in claim 1, wherein said hardened oil is selected from the group consisting of hardened castor oil, hardened rape oil and hardened soybean oil.

5. A granule as claimed in claim 1, wherein said intermediate layer consists essentially of said hardened oil and said cellulose.

6. A granule as claimed in claim 1, wherein a nonpareil seed is enclosed by said slow-release layer.

7. A multi-layer granule comprising an inner slow-release layer containing a pharmacologically effective ingredient and adapted to release said pharmacologically effective ingredient at a first rate; an outer fast-release layer containing a pharmacologically effective ingredient and adapted to release said pharmacologically effective ingredient at a second rate which is greater than said first rate; and an intermediate layer provided between and in contact with said slow-release layer and said fast-release layer, said intermediate layer comprising 20 to 90 percent by weight of a hardened oil selected from the group consisting of hardened castor oil, hardened rape oil and hardened soybean oil and 1 to 10 percent by weight of a cellulose selected from the group consisting of hydroxypropyl cellulose and methyl cellulose.

8. A granule as claimed in claim 7, wherein a nonpareil seed is enclosed by said slow-release layer.

9. A granule as claimed in claim 7, wherein said intermediate layer additionally comprises one or more members selected from the group consisting of a sucrose-fatty acid ester, talc and ethyl cellulose.

* * * * *